United States Patent [19]
Hollingsworth et al.

[11] Patent Number: 6,084,131
[45] Date of Patent: Jul. 4, 2000

[54] PROCESS FOR THE PREPARATION OF PROTECTED DIHYDROXYPROPYL TRIALKYLAMMONIUM SALTS AND DERIVATIVES THEREOF

[75] Inventors: Rawle I. Hollingsworth, Haslett; Guijun Wang, East Lansing, both of Mich.

[73] Assignee: Board of Trustees operating Michigan State University, East Lansing, Mich.

[21] Appl. No.: 09/321,220

[22] Filed: May 27, 1999

Related U.S. Application Data

[60] Provisional application No. 60/087,433, Jun. 1, 1998.

[51] Int. Cl.$^7$ ............ C07C 209/12; C07C 303/30; C07D 317/28
[52] U.S. Cl. ............ 564/296; 558/45; 558/47; 558/48; 558/136; 558/166; 549/451; 549/452; 560/253; 564/292
[58] Field of Search .................... 549/451, 452; 560/253; 564/292, 296; 558/45, 47, 48, 136, 166

[56] References Cited

U.S. PATENT DOCUMENTS

| | | |
|---|---|---|
| 2,666,783 | 1/1954 | Lytton ................... 564/292 |
| 3,813,441 | 5/1974 | Muller-Schiedmayer ........ 564/296 |
| 4,594,452 | 6/1986 | Reimschuessel ............ 564/292 |
| 4,814,506 | 3/1989 | Katayama et al. . |
| 5,077,435 | 12/1991 | Kimbrell et al. . |
| 5,292,939 | 3/1994 | Hollingsworth . |
| 5,319,110 | 6/1994 | HOllingsworth . |
| 5,374,773 | 12/1994 | Hollingsworth . |
| 5,808,107 | 9/1998 | Hollingsworth . |

OTHER PUBLICATIONS

Takemura, Chem Abstr. 101:203881, 1984.

Morishita et al., Chem Abst. 109:92507, 1988.

*Primary Examiner*—Peter O'Sullivan
*Attorney, Agent, or Firm*—Ian C. McLeod

[57] ABSTRACT

A process for the preparation of protected dihydroxypropyl trialkylammonium salts, particularly in chiral form is described. In particular, a process for the preparation of (2,2-dimethyl-1,3-dioxolan-4-ylmethyl)trialkylammonium salts, particularly in chiral form is described. Furthermore, a process is described wherein the (2,2-dimethyl-1,3-dioxolan-4ylmethyl)trialkylammonium salts is a 2,2-dimethyl-1,3-dioxolan-4-ylmethyl trimethylammonium salt, preferably in chiral form. The protected dihydroxypropyl trialkylammonium salts lead to L-carnitine (9) when in chiral form (5).

32 Claims, 1 Drawing Sheet

PROCESS FOR THE PREPARATION OF PROTECTED DIHYDROXYPROPYL TRIALKYLAMMONIUM SALTS AND DERIVATIVES THEREOF

CROSS-REFERENCE TO RELATED APPLICATION

This application claims priority to U.S. Provisional Application Ser. No. 60/087,433, filed Jun. 1, 1998.

STATEMENT REGARDING FEDERALLY SPONSORED RESEARCH OR DEVELOPMENT

This invention was supported in part by a United States Department of Energy Grant No. DE-FG02-89ER14029. The U.S. government has certain rights in this invention.

BACKGROUND OF THE INVENTION

(1) Field of the Invention

The present invention relates to a process for the preparation of protected trialkylammonium salts, particularly in chiral form. The trimethylammonium salts are particularly useful in the preparation of L-carnitine, a key intermediate for pharmaceutical compounds. In particular, the present invention relates to a process for the preparation of (2,2-dimethyl-1,3-dioxolan-4-ylmethyl)trialkylammonium salts, particularly in chiral form.

(2) Description of Related Art

L-carnitine is a key intermediate for the preparation of many pharmaceutical compounds. 1,2-dihydroxypropyl trimethylammonium salts 6 (see Scheme 1) have been employed in two routes to L-carnitine. The use of this intermediate is not of industrial significance, however, because of the substantial cost of the key optically pure 3-carbon starting materials, epichlorohydrin and chlorodihydroxy propane. In the first synthesis, (S)-epichlorohydrin is treated with trimethylamine to form (S)-1-chloro-2-hydroxypropyltrimethylammonium sulfate. This is then converted to a nitrile by displacement of the chloro group with cyanide. Hydrolysis yields L-carnitine 9 as shown in Scheme 3 (Reimschuessel et al, U.S. Pat. No. 4,594,452 (1986); Kimbrell and Russell, U.S. Pat. No. 5,077,435 (1991)). In the other synthesis route, treatment of (R)-1-chloro-2,3-dihydroxypropane with trimethylamine produces 1,2-dihydroxypropyl trimethylammonium salts which structure is shown by 6 in Scheme 1. The diol 6 is then converted to (S)-3-chloro-2-hydroxypropyl trimethylammonium chloride by treatment with thionyl chloride. This is then hydrolyzed to yield L-carnitine (Katayama et al., U.S. Pat. No. 4,814,506 (1989)). There is a need for an economical and reliable process.

SUMMARY OF THE INVENTION

The present invention relates to a process to produce protected dihydroxypropyl trialkylammonium salts which comprises reacting in a reactive mixture protected 3-amino-1,2-dihydroxypropane with a lower alkylating agent in the presence of a base in a solvent for the reaction mixture to produce the protected dihydroxypropyl trialkylammonium salt. In a preferred embodiment, the process produces a protected dihydroxypropyl trimethylammonium salt.

In particular, the present invention relates to a process to produce (2,2-dimethyl-1,3-dioxolan-4-ylmethyl)trialkylammonium salts which comprises reacting in a reactive mixture 3-amino-1,2-dihydroxypropane isopropylidene acetal with a lower alkylating agent in the presence of a base in a solvent for the reaction mixture to produce the 2,2-dimethyl-1,3-dioxolan-4-ylmethyl)trialkylammonium salt. Further, the present invention relates to a process for preparing (2,2-dimethyl-1,3-dioxolan-4-ylmethyl) trimethylammonium salt in a reaction mixture containing 3-amino-1,2-dihydroxypropane isopropylidene acetal.

The present invention further relates to a process for the preparation of the protected dihydroxypropyl trialkylammonium salt from (S)-3-hydroxy-γ-butyrolactone. In particular, the present invention provides a process for the preparation of the (2,2-dimethyl-1,3-dioxolan-4-ylmethyl) trimethylammonium salt.

The present invention also relates to the preparation of 1,2-dihydroxypropyl-3-trimethylammonium salts from the protected dihydroxypropyl trimethylammonium salt.

The present invention further relates to a process for the preparation of L-carnitine from the protected dihydroxypropyl trialkylammonium salt.

OBJECTS

It is an object of the present invention to provide a novel process for producing protected dihydroxypropyl trialkylammonium salts. In particular, it is an object of the present invention to provide protected trimethylammonium salts which are key intermediates in producing carnitine, particularly in chiral form. In particular the present invention relates to a process which is simple and economical. These and other objects will become increasingly apparent by reference to the following description and the drawing.

DESCRIPTION OF PREFERRED EMBODIMENTS

Figure 1:
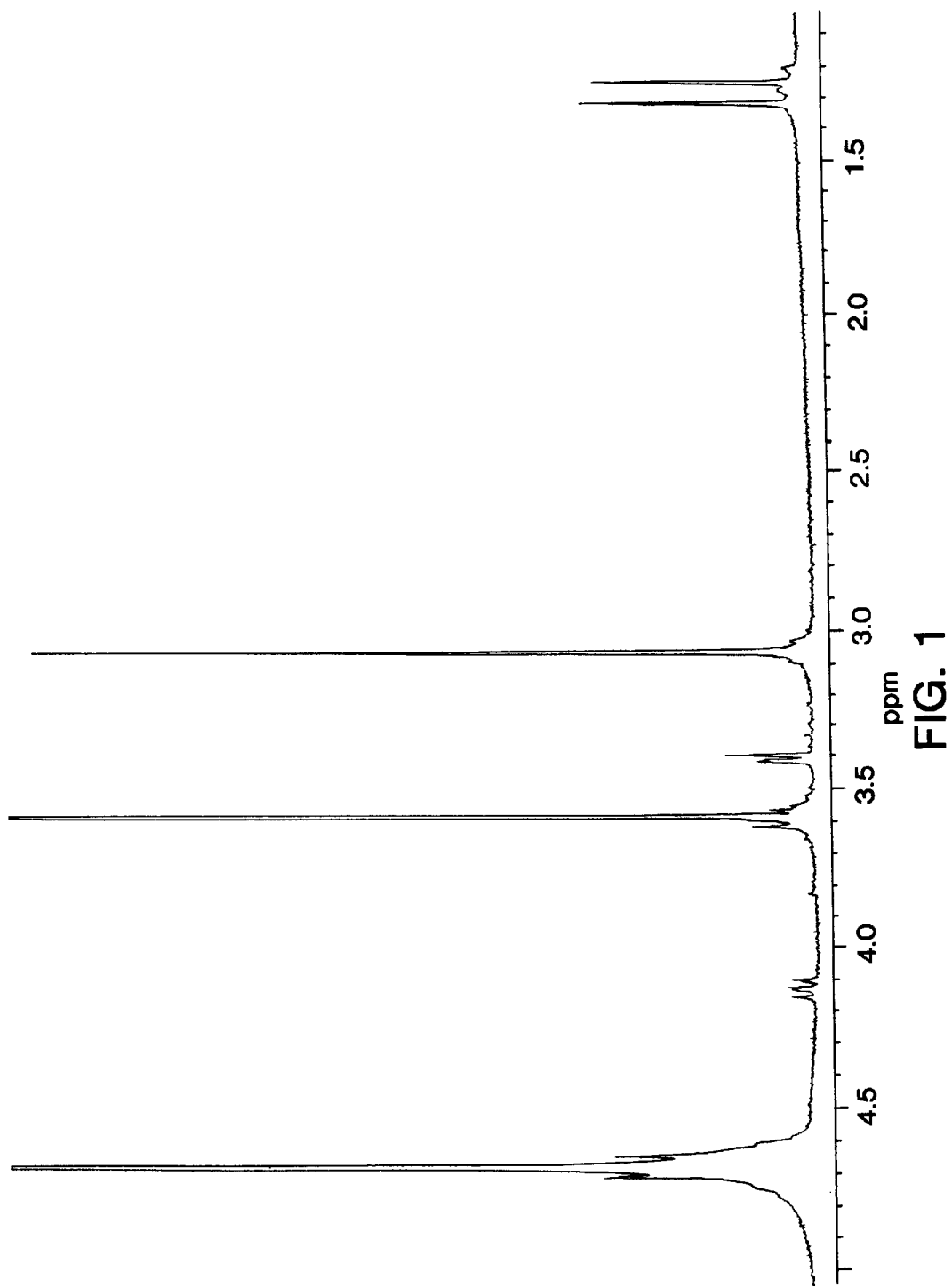
FIG. 1 is a graph showing a proton NMR ($^1$HNMR) for (2,2-dimethyl-1,3-dioxolan-4-ylmethyl) trimethylammonium 5 (1,2-dihydroxy-3-trimethylammonium propane isopropylidene acetal) as shown in Scheme 2.

The present invention relates to a process shown in Scheme 1 for producing in a reaction mixture a protected dihydroxypropyl trialkylammonium salt, having the formula:

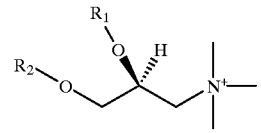

wherein $R_1$ and $R_2$ are protecting groups which can be combined which comprises reacting a protected 3-amino-1,2-dihydroxypropane salt in a reaction mixture, having the formula:

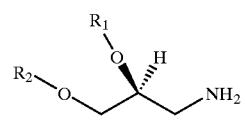

wherein $R_1$ and $R_2$ are the same protecting groups with a lower alkylating agent in the presence of a base in a solvent for the reaction mixture to produce the protected dihydroxypropyl trialkylammonium salt.

In the process to produce the protected dihydroxypropyl trialkylammonium salt, the alkylating agent is methyl halide which produces a protected dihydroxypropyl trimethylammonium salt. In one embodiment of the process, the methyl halide is methyl iodide which produces the protected dihydroxypropyl trimethylammonium iodide. In another embodiment, the alkylating agent is dimethylsulfate which produces the protected dihydroxypropyl trimethylammonium sulfate. In the preferred process, the base is sodium hydroxide. In the preferred process, the solvent is aqueous methanol.

In the process to produce the protected dihydroxypropyl trialkylammonium salt, the protecting group is selected from the group consisting of alkyloxy, aryloxy, acyloxy, halo, sulfonyloxy, sulfate, phosphate, saccharide and combinations thereof. Furthermore, in the process, the protecting group is an acetal selected from the group consisting of alkylidene, arylidene, acylidene and combinations thereof. In the preferred process, the protecting group is a geminal dimethoxy-acetal such as 2,2-dimethylsulfate which is 1,2-dihydroxy-3-trialkyammoniumpropane isopropylidene acetal.

In the process to produce the protected dihydroxypropyl trialkylammonium salt, the inorganic bases are preferably sodium or potassium hydroxide or sodium or potassium carbonate. The alkylating agent is an alkyl halide (Br, I, Cl, F) sulfate, tosylate or sulfonate. The solvent is preferably water or a lower alkanol (1 to 4 carbon atoms), most preferably methanol. The reaction is conducted at 10° to 70° C., optimally 25° to 50° C.

In a preferred process to produce the protected dihydroxypropyl trialkylammonium salt, the protected 3-amino-1,2-dihydroxypropane is produced in a reaction mixture from a protected butyramide having the formula:

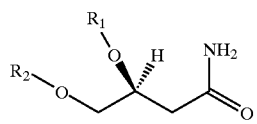

wherein $R_1$ and $R_2$ are protecting groups which can be combined wherein the reaction mixture is a Hoffman rearrangement reaction which contains a base and a halogen to produce the protected 3-amino-1,2-dihydroxypropane. The protected butyramide is produced from 3,4-dihydroxybutyramide in a reactive mixture comprising an acid and the protecting group in a solvent for the reaction.

The present invention further provides a process for preparing a protected dihydroxypropyl trialkylammonium salt from 3-hydroxy-γ-butyrolactone. The process comprises the steps of (1) reacting 3-hydroxy-γ-butyrolactone with ammonia hydroxide to produce 3,4-dihydroxybutyramide; (2) reacting the 3,4-dihydroxybutyramide with a protecting group to produce a protected butyramide; (3) reacting the protected butyramide in a Hoffman rearrangement reaction containing a base and sodium hypochlorite to produce a protected 3-amino-1,2-dihydroxypropane; and (4) reacting the protected 3-amino-1,2-dihydroxypropane with an alkylating agent in the presence of a base in a solvent for the reaction to produce the protected dihydroxypropyl trialkylammonium salt.

In the process for preparing a protected trialkylammonium salt from 3-hydroxy-γ-butyrolactone, the alkylating agent in step (4) is methyl halide which produces the protected dihydroxypropyl trialkylammonium salt which is a protected dihydroxypropyl trimethylammonium salt. In a preferred process to produce the protected dihydroxypropyl trialkylammonium salt, the methyl halide is methyl iodide which results in the production of a protected dihydroxypropyl trimethylammonium iodide. In an alternate process to produce the protected dihydroxypropyl trimethylammonium salt, the alkylating agent is dimethylsulfate which results in the production of a protected dihydroxypropyl trimethylammonium sulfate.

In the process for preparing a protected trialkylammonium salt from 3-hydroxy-γ-butyrolactone, the protecting group added to the 1 and 2 hydroxy groups of 3,4-dihydroxybutyramide to produce the protected butyramide is 2,2-dimethoxypropane.

The present invention preferably relates to a process which comprises reacting in a reactive mixture 3-amino-1,2-dihydroxypropane isopropylidene acetal with a lower alkylating agent in the presence of a base in a solvent for the reaction mixture to produce a (2,2-dimethyl-1,3-dioxolan-4-ylmethyl)trialkylammonium salt. In particular, the present invention relates to the preparation of (2,2-dimethyl-1,3-dioxolan-4-ylmethyl)trimethylammonium salt.

In the process to produce the (2,2-dimethyl-1,3-dioxolan-4-ylmethyl)trialkylammonium salt from 3-amino-1,2-dihydroxypropane isopropylidene acetal, the alkylating agent is methyl halide. In one embodiment, the methyl halide is methyl iodide which produces the (2,2-dimethyl-1,3-dioxolan-4-ylmethyl)trialkylammonium salt which is a (2,2-dimethyl-1,3-dioxolan-4-ylmethyl) trimethylammonium iodide. In another embodiment, the alkylating agent is dimethylsulfate which produces the (2,2-dimethyl-1,3-dioxolan-4-ylmethyl)trialkylammonium salt which is a (2,2-dimethyl-1,3-dioxolan-4-ylmethyl) trimethylammonium sulfate. In the preferred process, the base is sodium hydroxide. In the preferred process, the solvent is aqueous methanol.

In the process to produce the (2,2-dimethyl-1,3-dioxolan-4-ylmethyl)trialkylammonium salt from 3-amino-1,2-dihydroxypropane isopropylidene acetal, the inorganic bases are preferably sodium or potassium hydroxide or sodium or potassium carbonate. The alkylating agent is an alkyl halide (Br, I, Cl, F), sulfate, tosylate or sulfonate. The solvent is preferably water or a lower alkanol (1 to 4 carbon atoms), most preferably methanol. The reaction is conducted at 10° to 70° C., optimally 25° to 50° C.

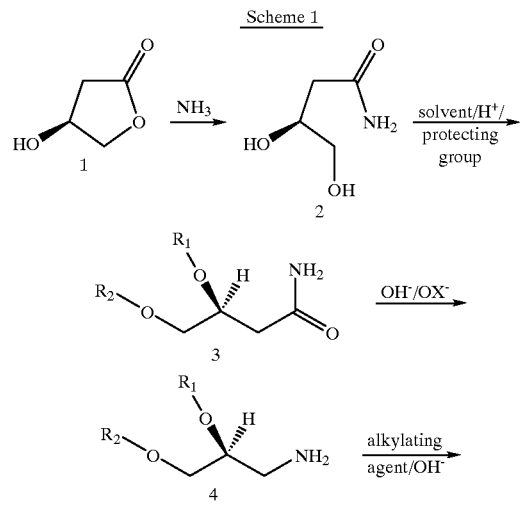

-continued

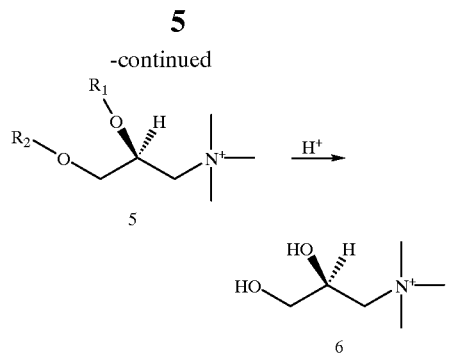

Scheme 1 shows the synthesis of a protected dihydroxypropyl trimethylammonium salt (5) from 3-hydroxy-γ-butyrolactone (1). In Scheme 1, $R_1$ and $R_2$ are any protecting groups which can be different or combined and X is any halogen such as chlorine, bromine, fluorine, or iodine. In the reaction, 1 is converted to 3,4-dihydroxybutyramide (2) in a reaction with ammonium hydroxide at room temperature. After removal of water, 2 is converted to the protected butyramide (3) in a reaction mixture containing a protecting group and an acid in a solvent. This reaction is quantitative and produces the protected butyramide (3) which can be crystallized upon concentration to dryness. A Hoffman rearrangement reaction completely converts 3 to a protected 3-amino-1,2-dihydroxypropane (4) which is then converted to a protected dihydroxypropyl trialkylammonium salt (5) in a reaction consisting of an alkylating agent in the presence of a base. Alkylating agents suitable for the conversion include methyl halides such as methyl iodide or dimethyl sulfate. The reaction essentially converts all of 4 to 5. The protected dihydroxypropyl trialkylammonium salt (5) can be converted in the presence of an acid to the 3,2-dihydroxypropyl trialkylammonium salt (6) by removal of the protecting groups. Alternatively, 5 is converted to carnitine (9) as shown in Scheme 3.

The important step in obtaining 5 is a 1-carbon chain descension step in which the 4-carbon intermediate (3) is stereospecifically and quantitatively converted to the pure 3-carbon primary amine (4) via a Hoffman rearrangement reaction on the protected amide (3). In a Hoffman rearrangement reaction, primary amines react with Cl or Br in the presence of a strong base to form amines with the loss of the carbonyl carbon atom. However, such a reaction on a γ-hydroxyamide normally fails because of participation by the alcohol function to form a lactone.

One important aspect of this invention is that participation of the alcohol functions can be avoided by tying up the interfering alcohol functions with blocking or protecting groups. The 3 and 4 hydroxyl groups of the dihydroxybutyramide (2) can be protected with any combination of protecting groups which includes but is not limited to the constituents of the group consisting of alkyloxy, aryloxy, acyloxy, halo, sulfonyloxy, sulfate, phosphate or saccharide. Protected butyramide (3), protected 3-amino-1,2-dihydroxypropane (4), and protected dihydroxypropyl trialkylammonium salts (5) are shown wherein $R_1$ and $R_2$ are protecting groups. The protecting groups ($R_1$ and $R_2$) form acetals which can be the same or combined when the protecting group is a geminal dimethoxy acetal. Thus, the protecting groups can be any combination of alkylidene, arylidene or acylidene groups which includes such acetals such as propylidene, benzylidene, ethylidene and methylidene. In a preferred embodiment, the protecting group is a geminal dimethoxy-acetal such as 2,2-dimethoxypropane which forms a cyclic acetal with the 3 and 4 hydroxyl groups of the dihydroxybutyramide (2) to form the protected dihydroxybutyramide (3a in Scheme 2). The use of methyl iodide, chloride, fluoride, or bromide in the conversion of 4 to 5 yields the corresponding halide salts of 5 directly. Alternatively, the use of dimethylsulfate gives the methylsulfate salts of 5 directly. This can be exchanged with an ion exchange resin for hydroxide or halide counter ions.

The use of (S)-3-hydroxy-γ-butyrolactone (1) as the starting material for synthesis of 5 is convenient over prior art methods because 1 can be synthesized in high yield and in large quantities from renewable, natural resources. Inexpensive methods for synthesizing 1 have been described in: U.S. Pat. No. 5,319,110 to R. Hollingsworth which discloses a process for synthesis of an internal cyclic ester such as a lactone by converting a hexose source, which contains hexose as a substituent and another sugar attached to the hexose substituent in the 4 position via (S)-3,4-dihydroxybutanoic acid as an intermediate; U.S. Pat. No. 5,374,773 to R. Hollingsworth which discloses a process for the synthesis (S)-3,4-hydroxybutanoic salt by converting a hexose source which contains hexose as a substituent and another sugar attached to the hexose substituent in the 4 position via (S)-3,4-dihydroxybutyric acid as an intermediate; U.S. Pat. No. 5,292,939 to R. Hollingsworth which discloses synthesis of (S)-3,4-dihydroxybutyric acid from substituted D-hexose; and U.S. Pat. No. 5,808,107 to R. Hollingsworth which discloses another process for producing chiral lactones. These references are herein incorporated by reference.

In a preferred process to produce the (2,2-dimethyl-1,3-dioxolan-4-ylmethyl)trialkylammonium salt from 3-amino-1,2-dihydroxypropane isopropylidene acetal, (S)-3-dihydroxybutanoic acid-γ-lactone (1) or its free acid is converted to a (S)-(2,2-dimethyl-1,3-dioxolan-4-ylmethyl) trialkylammonium salt (5a) as shown in Scheme 2. This protected form of (S)-1,2-dihydroxypropyl-3-trialkylammonium salts, is an intermediate for which synthetic routes with conversions in good yields to L-carnitine exist. The (S)-(2,2-dimethyl-1,3-dioxolan-4-ylmethyl) trimethylammonium salt (5a in scheme 2) can be easily converted into carnitine (9) in a few steps as shown in scheme 3. The trimethylamino dioxolane (5a) can also be converted to the corresponding diol (6) by acid hydrolysis.

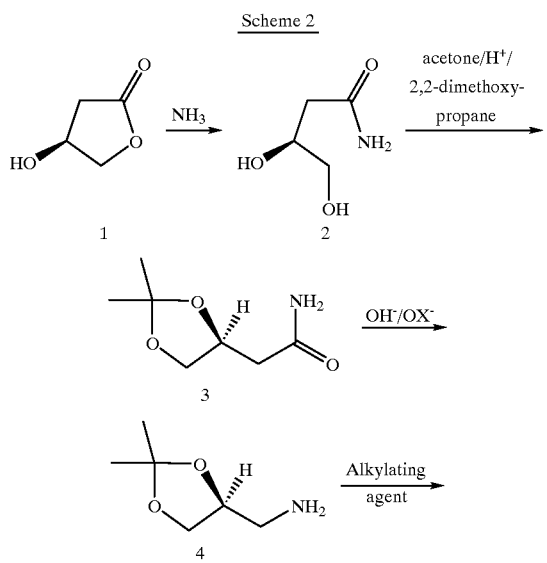

-continued

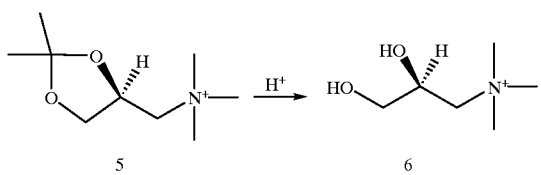

Scheme 3

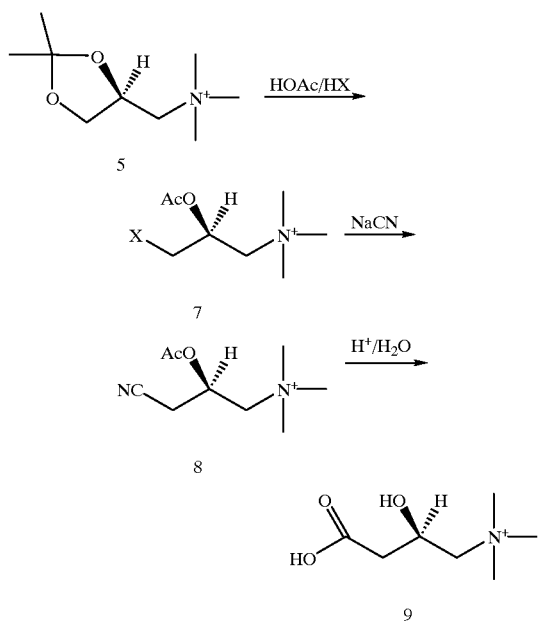

Scheme 2 shows the synthesis of a (2,2-dimethyl-1,3-dioxolan-4-ylmethyl)trimethylammonium salt (5a) (1,2-dihydroxy-3-trimethylammonium propane isopropylidene acetal) from 3-hydroxy-γ-butyrolactone (1). In Scheme 2, X is a halogen such as Br, I, F, or Cl. In the reaction, 1 is converted to 3,4-dihydroxybutyramide (2) in a reaction with ammonium hydroxide at room temperature. After removal of water, 2 is converted to the protected butyramide (3a) in a reaction mixture containing a protecting group such as 2,2-dimethoxypropane, and an acid in a solvent such as acetone. This reaction is quantitative and produces the protected butyramide (3a) which can be crystallized upon concentration to dryness. A Hoffman rearrangement reaction completely converts 3a to 3-amino-1,2-dihydroxypropane isopropylidene acetal (4a) which is then converted to (2,2-dimethyl-1,3-dioxolan-4-ylmethyl)trimethylammonium salt (5a) in a reaction consisting of an alkylating agent in the presence of a base. Alkylating agents suitable for the conversion include methyl halides such as methyl iodide or dimethyl sulfate. The reaction essentially converts all of 4a to 5a. 2,2-dimethyl-1,3-dioxolan-4-ylmethyl) trialkylammonium salt (5a) is converted in the presence of an acid to the 1,2-dihydroxypropyl trialkylammonium salt (6) by removal of the protecting groups.

This reaction sequence has several advantages over the prior art. First, it avoids the use of optically pure epichlorohydrin which is very costly. Second, gaseous trimethylamine is not used. Third, synthesis starts from (S)-3-hydroxy-γ-butyrolactone (1) which is easily available, in high yield with high optical purity from starch, lactose and a variety of readily available and cheap carbohydrate raw materials. The (S)-1,2-dihydroxypropyl trialkylammonium salt (6) is obtained cleanly and efficiently from the protected amide (3 or 3a) which is, in turn, obtained quantitatively from (S)-3-hydroxy-γ-butyrolactone (1). This route provides an economically viable path to the commercial production of L-carnitine (9).

(2,2-dimethyl-1,3-dioxolan-4-ylmethyl) trialkylammonium salt 5a is a precursor for the synthesis of compounds such as L-carnitine. For example, in Scheme 3, L-carnitine (9) is synthesized from 5a. In a reaction consisting of HOAc and a halide, 5a is converted to 1-halo-2-oxyacetyl-propyl trimethylammonium salt (7). Then, in a nucleophilic substitution reaction, the halogen atom in 7 is replaced by a cyanide ion to make 1-nitrile-2-oxyacetyl-propyl trialkylammonium salt (8) which is then, in the presence of an acid, is converted to L-carnitine (9).

(S)-1,2-dihydroxypropyl trialkylammonium salt (6) is also a precursor for other compounds such as L-carnitine (9). To make L-carnitine, the primary hydroxyl of 6 is selectively halogenated to produce the compound, 1-halo-2-hydroxypropyl trialkylammonium salt, which is then converted to 3-nitrile-2-hydroxypropane trialkylammonium salt in a nucleophilic reaction with sodium cyanide. Then, the 3-nitrile-2-hydroxypropane trimethylammonium salt is converted to L-carnitine (9) in the presence of an acid. In U.S. Pat. No. 4,814,506 to Katayana et al, the synthesis of L-carnitine, 6 is an intermediate made from (R)-1-chloro-2,3-propanediol wherein the (R)-1-chloro-2,3-propanediol is recovered from a racemic mixture of the (R) and (S) forms treated with a microorganism which selectively metabolizes the (S) form. In contrast to the prior art, the present invention provides an economical method for preparing 6 from 3-hydroxy-γ-butyrolactone.

The following examples are intended to promote a further understanding of the present invention.

EXAMPLE 1

This Example shows the process for the preparation of (2,2-dimethyl-1,3-dioxolan-4-ylmethyl) trimethylammonium sulfate (5) from (S)-3-hydroxy-γ-butyrolactone (1).

(S)-3-hydroxy-γ-butyrolactone (1) (51 g, 0.5 mol) was converted to the amide (2) by treatment at room temperature for 14 hours with 110 ml of 30% ammonium hydroxide (0.85 mol). The solution was then concentrated to a syrup at ~50° C. under reduced pressure until no more water could be removed. Acetone (500 mL) and 2,2-dimethoxypropane (104 g, 1 mol) was added. Sulfuric acid (2 mL) was then added and the mixture protected from moisture with a calcium chloride drying tube, heated at 60° C. for 30 minutes and stirred at room temperature for 12 hours. Silver oxide (20 g) was added and the mixture stirred for 1 hour. Methanol (200 ml) was then added and the mixture filtered and concentrated to dryness. The protected amide (3) was crystallized upon concentrating and was used directly in the next step. Conversion to the protected amide (3) was essentially quantitative. A small amount when recrystallized from acetone gave white crystals mp, 98–100° C. $[\alpha]_{589}$=−15.4 (CHCl$_3$, c=1), $^1$H-NMR (CDCl$_3$, 300 MHZ) δ 6.10 (s, 1H), 5.65 (s, 1H), 4.43 (m, 1H), 4.14 (dd, 1H, J=8.1 and 6.3 Hz) 3.63 (dd, 1H, J=8.1 and 6.8 Hz) 2.55 (dd, 1H, J=15.3 and 7.5 Hz), 2.46 (dd, 1H, J=15.3 and 4.8 Hz), 1.42 (s, 3H), 1.35 (s, 3H) $^{13}$C-NMR (CDCl$_3$ 75 MHZ) δ 172.86, 109.50, 72.21, 69.05, 40.07, 26.90, 25.50.

The protected amide (3) (0.08 g 0.005 mol) was treated with 10–12% sodium hypochlorite solution (5 ml) and the mixture stirred until all of the solid had dissolved (~5 mins).

Sodium hydroxide (0.8 grams dissolved in 5 ml water) was added to the mixture and the solution was warmed to 50–60° C. and then kept there for 24 hours by which time conversion to 3-amino-1,2-dihydroxypropane isopropylidene acetal (4) was completed. $^1$H-NMR spectroscopy indicated 100% conversion of 3 to 4.

In this process, 4 was not isolated but was directly converted to the trimethylamino derivative (5) by adding dimethyl sulfate (6 equivalents), sodium hydroxide (0.85 g, 0.021 moles) and 2 ml of methanol and stirring for a further (12 hours). Proton NMR spectroscopy (FIG. 1) clearly indicated complete conversion to (2,2-dimethyl-1,3-dioxolan-4-ylmethyl)trimethylammonium sulfate (5). The analysis showed the methine proton signal appeared as a triplet (J=~8 Hz) at 4.12 ppm, the methylene protons adjacent to the trimethylamino group was a doublet (J=~8 Hz) at 3.4 ppm and the signals for the methylene group on the dioxolane ring were partially obscured by the one for the methylsulfate anion at 3.59 ppm.

EXAMPLE 2

This Example shows a process for the preparation of the protected butyramide (3) from (S)-3-hydroxy-γ-butyrolactone (1). In this Example, 3 was recovered from the reaction mixture.

(S)-3-hydroxy-γ-butyrolactone (51 g, 0.5 mol) was converted to the amide (2) by treatment at room temperature for 14 hours with 110 ml of 30% ammonium hydroxide (0.85 mol). The solution was then concentrated to a syrup at ~50° C. under reduced pressure until no more water could be removed. Then, 500 ml of acetone and the blocking group 2,2-dimethoxypropane (104 g, 1 mol) was added. Sulfuric acid (2 ml) was then added and the mixture, protected from moisture with a calcium chloride drying tube, was heated at 60° C. for 30 minutes, and then stirred at room temperature for 12 hours. Afterwards, 20 g of silver oxide was added and the mixture stirred for an additional hour. Then, methanol (200 ml) was added to the mixture, which was then filtered and concentrated to dryness, wherein the protected butyramide (3) was crystallized.

Preparation of the protected butyramide (3) was essentially quantitative. A small amount was crystallized from acetone to give white crystals which had a melting point between 106 to 108° C. The protected butyramide (3) is used to synthesize compounds such as 3-amino-1,2-dihydroxypropane isopropylidene (4) and (2,2-dimethyl-1, 3-dioxolan-4-ylmethyl)trimethylammonium salts (5) which is used in the synthesis of carnitine (9) as shown in Scheme 3, 1,2-dihydroxypropyltrimethylammonium salts (6) which is be also used to synthesize carnitine.

EXAMPLE 3

This Example shows a process for the preparation of the 3-amino-1,2-dihydroxypropane isopropylidene (4) from protected butyramide (3) in a Hoffman rearrangement reaction. In this Example, 4 was recovered from the reaction mixture instead of converted to 5.

The 0.08 g (0.005 mol) of the protected amide (3) was treated with 10–12% sodium hypochlorite solution (5 ml) and the mixture was stirred until all of the solid had dissolved (~5 minutes). Sodium hydroxide (0.8 grams dissolved in 5 ml of water) was added to the mixture and the solution was warmed to 50 to 60° C. and kept there for 24 hours by which time conversion to 3-amino-1,2-dihydroxypropane isopropylidene (4) was completed. $^1$H-NMR spectroscopy indicated 100% conversion of (3) to (4).

3-amino-1,2-dihydroxypropane isopropylidene (4) is used in the synthesis of compounds such as (2,2-dimethyl-1,3-dioxolan-4-ylmethyl)trimethylammonium salts (5) as shown in Example 1, or 1,2-dihydroxypropyltrimethylammonium salts (6) which is also be used to synthesize carnitine.

EXAMPLE 4

This Example shows a process for the preparation of L-carnitine (9) from (S)-(2,2-dimethyl-1,3-dioxolan-4-ylmethyl)trimethylammonium salts (5).

S-(2,2-dimethyl-1,3-dioxolan-4-ylmethyl) trimethylammonium salt is reacted with HOAc and the halogenating reagent, hydrogen bromide, to produce (S)-1-bromo-2-oxyacetyl-propane trimethylammonium acetal (7). Alternatively, the halogenating reagent can be thionyl chloride. The bromine is displaced by reacting 7 with NaCN to produce the nitril intermediate (8) which is then converted in the presence of an acid to L-carnitine (9).

EXAMPLE 5

This Example shows a process for the preparation of L-carnitine (9) from 1,2-dihydroxypropane trimethylammonia salt (6). (S)-1,2-dihydroxypropane trimethylammonium salt (6) is converted to (S)-3-bromo-2-hydroxypropane trimethylammonium salt by halogenation with hydrogen bromide. The bromine is displaced by reacting (S)-1-bromo-2-hydroxypropane trimethylammonium salt with sodium prussiate (NaCN) to produce the nitrile intermediate which is then converted in the presence of an acid to L-carnitine (9). Alternatively, halogenation of 6 can be achieved using thionyl chloride.

It is intended that the foregoing description be only illustrative of the present invention and that the present invention be limited only by the hereinafter appended claims.

We claim:

1. A process for preparing a protected dihydroxypropyl trialkylammonium salt, having the formula:

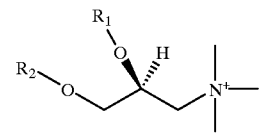

wherein $R_1$ and $R_2$ are protecting groups which can be combined which comprises:

(a) reacting a protected butyramide having the formula:

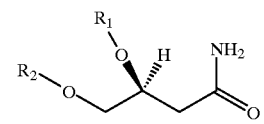

wherein $R_1$ and $R_2$ are the same protecting groups which can be combined in a reaction mixture in a Hoffman rearrangement reaction with a base and a halogen to produce a protected 3-amino-1,2-dihydroxypropane having the formula:

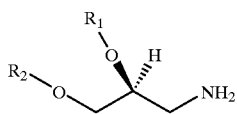

wherein $R_1$ and $R_2$ are the same protecting groups which can be combined; and (b) reacting the protected 3-amino-1,2-dihydroxypropane with a lower alkylating agent in the presence of a base in a solvent for the reaction mixture to produce the protected dihydroxypropyl trialkylammonium salt.

2. The process of claim 1 wherein the alkylating agent is methyl halide to produce the protected dihydroxypropyl trialkylammonium salt which is a protected dihydroxypropyl trimethylammonium salt.

3. The process of claim 1 wherein the methyl halide is methyl iodide to produce the protected dihydroxypropyl trialkylammonium salt which is a protected dihydroxypropyl trimethylammonium iodide.

4. The process of claim 1 wherein the alkylating agent is dimethylsulfate to produce the protected dihydroxypropyl trialkylammonium salt which is a protected dihydroxypropyl trimethylammonium sulfate.

5. The process of any one of claims 1, 2, 3, or 4 wherein the base is sodium hydroxide.

6. The process of any one of claims 1, 2, 3, or 4 wherein the solvent is an aqueous alcohol.

7. The process of claim 1 wherein the protecting group is selected from the group consisting of alkyl, aryl acyl sulfonate, phosphonate [sulfonyloxy, sulfate, phosphate,] saccharide and combinations thereof.

8. The process of claim 1 wherein the protecting group is an acetal selected from the group consisting of alkylidene, arylidene, acylidene and combinations thereof.

9. The process of claim 1 wherein the protecting group is an isopropylidene acetal.

10. The process of claim 1 wherein the protected butyramide is produced from 3,4-dihydroxybutyramide in a reactive mixture comprising an acid and a protecting group in a solvent for the reaction to produce the protected butyramide.

11. A process for preparing a protected dihydroxypropyl trialkylammonium salt which comprises:

(a) reacting 3-hydroxy-γ-butyrolactone with ammonia hydroxide to produce 3,4-dihydroxybutyramide;

(b) reacting the 3,4-dihydroxybutyramide with a protecting group to produce a protected butyramide;

(c) reacting the protected butyramide in a Hoffman rearrangement reaction containing a base and sodium hypochlorite to produce protected 3-amino-1,2-dihydroxypropane; and (d) reacting the protected 3-amino-1,2-dihydroxypropane with an alkylating agent in the presence of a base in a solvent for the reaction to produce the protected dihydroxypropyl trialkylammonium salt.

12. The process of claim 11 wherein the alkylating agent in step (d) is methyl halide to produce the protected dihydroxypropyl trialkylammonium salt which is a protected dihydroxypropyl trimethylammonium salt.

13. The process of claim 11 wherein the methyl halide is methyl iodide to produce the protected dihydroxypropyl trialkylammonium salt which is a protected dihydroxypropyl trimethylammonium iodide.

14. The process of claim 11 wherein the alkylating agent in step (d) is dimethylsulfate to produce the protected dihydroxypropyl trialkylammonium salt which is a protected dihydroxypropyl trimethylammonium sulfate.

15. The process of any one of claims 11, 12, 13, or 14 wherein the base is sodium hydroxide.

16. The process of any one of claims 11, 12, 13, or 14 wherein the solvent is an aqueous alcohol.

17. The process of claim 12 wherein the protecting group is 2,2-dimethoxypropane.

18. A process which comprises:

(a) reacting an isopropylidene protected acetal butyramide with a base and a halogen in a Hoffman rearrangement reaction to produce a 3-amino-1,2-dihydropropane isopropylidene acetal;

(b) reacting in a reactive mixture the 3-amino-1,2-dihydroxypropane isopropylidene acetal with a lower alkylating agent in the presence of a base in a solvent for the reaction mixture to produce (2,2-dimethyl-1,3-dioxolan-4-ylmethyl)trialkylammonium salt.

19. The process of claim 18 wherein the alkylating agent is a methyl halide to produce the (2,2-dimethyl-1,3-dioxolan-4-ylmethyl)trialkylammonium salt which is a (2,2-dimethyl-1,3-dioxolan-4-ylmethyl)trimethylammonium salt.

20. The process of claim 19 wherein the methyl halide is methyl iodide to produce the (2,2-dimethyl-1,3-dioxolan-4-ylmethyl)trialkylammonium salt which is a (2,2-dimethyl-1,3-dioxolan-4-ylmethyl)trimethylammonium iodide.

21. The process of claim 18 wherein the alkylating agent is methyl sulfate to produce the (2,2-dimethyl-1,3-dioxolan-4-ylmethyl)trialkylammonium salt which is a (2,2-dimethyl-1,3-dioxolan-4-ylmethyl)trimethylammonium sulfate.

22. The process of any one of claims 18, 20, 21, wherein the solvent is an aqueous alcohol.

23. The process of any one of claims 18, 20, 21, wherein the base is sodium hydroxide.

24. The process of claim 18 wherein the 3-amino-1,2-dihydroxypropane isopropylidene acetal is prepared from 3-hydroxybutyrolactone reacted with ammonia, then reacted with acetone, acid and 2,2-dimethoxypropane, then reacted with base and sodium hypochlorite solution.

25. The process of any one of claims 18, 20 or 24 wherein the (2,2-dimethyl-1,3-dioxolan-4-ylmethyl) trialkylammonium salt is chiral.

26. The process of claim 18 wherein in addition the (2,2-dimethyl-1,3-dioxolan-4-ylmethyl)trialkylammonium salt is reacted with an acid to produce 2,3-dihydroxypropane trialkylammonium salt.

27. The process of claim 18 wherein the (2,2-dimethyl-1,3-dioxolan-4-ylmethyl)trialkylammonium salt is (2,2-dimethyl-1,3-dioxolan-4-ylmethyl)trimethylammonium salt which is reacted with an acid to produce 1,2-dihydroxypropyl trimethylammonium salt.

28. The process of claim 18 wherein the 1,2-dihydroxypropyl trimethylammonium salt is chiral.

29. The process of claim 1 wherein in addition the protected dihydroxypropyl trialkylammonium salt is reacted with an acid to produce the dihydroxypropyl trialkylammonium salt.

30. A process for preparing a protected dihydroxypropyl trialkylammonium salt, having the formula:

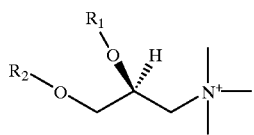

wherein $R_1$ and $R_2$ are protecting groups which can be combined which comprises:

(a) reacting a protected butyramide having the formula:

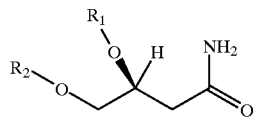

wherein $R_1$ and $R_2$ are the same protecting groups which can be combined in a reaction mixture in a Hoffman rearrangement reaction with a base and a halogen to produce the protected 3-amino-1,2-dihydroxypropane; and (b) reacting the protected 3-amino-1,2-dihydroxypropane, having the formula:

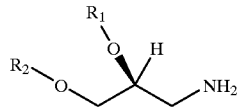

wherein $R_1$ and $R_2$ are the same protecting groups which can be combined, in a reaction mixture with a lower alkylating agent in the presence of a base in a solvent for the reaction mixture to produce the protected dihydroxypropyl trialkylammonium salt.

31. A process which comprises:

(a) reacting in a reactive mixture 3-amino-1,2-dihydroxypropane isopropylidene acetal with a lower alkylating agent in the presence of a base in a solvent for the reaction mixture to produce (2,2-dimethyl-1,3-dioxolan-4-ylmethyl)trialkylammonium salt; and (b) reacting the (2,2-dimethyl-1,3-dioxolan-4-ylmethyl) trialkylammonium salt with an acid to produce 2,3-dihydroxypropane trialkylammonium salt.

32. A process which comprises:

(a) reacting a protected 3-amino-1,2-dihydroxypropane having the formula:

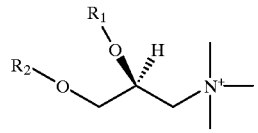

wherein $R_1$ and $R_2$ are protecting groups which can be combined, in a reaction mixture with a lower alkyl alkylating agent in the presence of a base in a solvent for the reaction mixture to produce a protected dihydroxypropyl trialkylammonium salt; and (b) reacting the protected dihydroxypropyl trialkylammonium salt with an acid to produce 2,3-dihydroxypropane trialkylammonium salt.

* * * * *

UNITED STATES PATENT AND TRADEMARK OFFICE
CERTIFICATE OF CORRECTION

PATENT NO.   : 6,084,131
DATED        : July 4, 2000
INVENTOR(S)  : Rawle I. Hollingsworth and Guijun Wang It is certified that error appears in the above-identified patent and that said Letters Patent is hereby corrected as shown below:

Column 7,
Line 36, the caption "Scheme 3" should be inserted below the structures.

Column 11,
Line 32, "[sulfonyloxy, sulfate, phosphate,] " should be deleted.

Column 12,
Line 8, "of Claim 12" should be -- of Claim 11 --.

Signed and Sealed this

Fourteenth Day of August, 2001

*Attest:*

*Attesting Officer*

NICHOLAS P. GODICI
*Acting Director of the United States Patent and Trademark Office*